United States Patent [19]
Lang et al.

[11] Patent Number: 5,587,174
[45] Date of Patent: Dec. 24, 1996

[54] COSMETIC COMPOSITION FOR TREATING SKIN AND HAIR CONTAINING APPLE WAX AND METHODS OF MAKING THEM

[75] Inventors: Günther Lang, Reinheim; Dieter Hoch, Pfungstadt-Eich; Eugen Konrad, Darmstadt; Wolfram Geibel, Hünfeld; Harald Wendel, Ober-Ramstadt; Thomas Kripp, Fränkisch-Crumbach, all of Germany

[73] Assignee: Wella Aktiengesellschaft, Darmstadt, Germany

[21] Appl. No.: 598,632

[22] Filed: Feb. 12, 1996

Related U.S. Application Data

[63] Continuation of Ser. No. 122,609, filed as PCT/EP93/00067, Jan. 14, 1993, abandoned.

[30] Foreign Application Priority Data

Feb. 28, 1992 [DE] Germany ............... 42 06 154.7

[51] Int. Cl.$^6$ ............... A61K 7/00; A61K 7/021; A61K 7/06

[52] U.S. Cl. ............... 424/401; 424/63; 424/70.1; 424/70.21; 424/70.22; 424/70.27; 424/70.31; 424/70.6; 514/844; 514/852

[58] Field of Search ............... 424/401, 63, 70.1, 424/70.21, 70.22, 70.27, 70.31, 70.6; 514/844, 852

[56] References Cited

U.S. PATENT DOCUMENTS

| | | | |
|---|---|---|---|
| 3,660,128 | 5/1972 | Sheldahl | 106/271 |
| 4,336,246 | 6/1982 | Leon Pekarek | 424/63 |
| 5,139,771 | 8/1992 | Gerstein | 424/63 |
| 5,194,260 | 3/1993 | Grollier et al. | 424/401 |

FOREIGN PATENT DOCUMENTS

| | | | |
|---|---|---|---|
| 53-044639 | 4/1978 | Japan | A61K 7/00 |
| 61-207321 | 9/1986 | Japan | A61K 7/06 |
| 1207218 | 8/1989 | Japan | A61K 7/00 |

OTHER PUBLICATIONS

Roempps Chemie–Lexikon, 8th Edition, Dr. Otto–Albrecht Newmueller, p. 2878 & 4563.

Kaufmann, et al, "XPS, an Analytical tool for the characterization of fibre surface modifications".

Food science & technology Abstracts, No. 79–11–H1846, "By–Products From Waste From Apple Juice Manufacture", G. M. Zaiko.

Lebensmittel–Wissenschaft Und Technologie, vol. 19, No. 6, 1986, pp. 493–496, Bundschu, et al, "Gewinnung von Natürlichen Aromen Aus Reststoffen . . . ".

Journal of the Science of Food and Agriculture, vol. 34, No. 11, 1973, pp. 1331–1336, Morice, et al, "Composition of the Surface Waxes of Apple Fruits . . . ".

*Primary Examiner*—Amy Hulina
*Attorney, Agent, or Firm*—Michael J. Striker

[57] ABSTRACT

The skin and hair treatment composition includes 0.5 to 2 percent by weight apple wax, 0.1 to 30 percent by weight of at least one anionic, cationic, amphoteric and/or nonionic surfactant, a solvent consisting of water, ethanol, propanol, isopropanol, glycols or mixtures thereof and one or more cosmetic additives selected from the group consisting of perfume oils; opacifiers; pearlescing agents; bacterial and fungicidal ingredients; coconut fatty acid diethanolamide; buffer substances; coloring materials; solubilizers; light stabilizers; antioxidants; complexing agents and antidandruff active ingredients. Methods for obtaining the apple wax used in these compositions include extraction of depectinized apple pomace with a variety of solvents and purification and evaporation of the extract to obtain an apple wax product.

3 Claims, No Drawings

COSMETIC COMPOSITION FOR TREATING SKIN AND HAIR CONTAINING APPLE WAX AND METHODS OF MAKING THEM

This application is a continuation of application Ser. No. 08/122,609, filed as PCT/EP93/00067, Jan. 14, 1993, now abandoned.

BACKGROUND OF THE INVENTION

The present invention relates to processes for obtaining apple wax, apple wax obtained by these processes and cosmetic compositions containing apple wax.

Waxes may perform a variety of functions in cosmetic compositions. For example, they can be used by themselves to cover the skin or as a fatty component in emulsions for improving the viscosity and stability of the cosmetic composition. In cosmetic compositions for the skin, waxes can be used to return oils to the skin and make it repellant to water and in cosmetic compositions for hair they can condition and groom the hair.

Based on production methods, waxes can be classified as natural, chemically modified natural, and synthetic. The important waxes for cosmetics include mineral waxes and certain natural waxes from animal or vegetable sources.

Natural and chemically modified natural mineral waxes come from nonrenewable raw material sources or are produced from raw materials generated from these sources. Synthetic mineral waxes are often loaded with impurities conditioned by synthesis.

The disadvantages of mineral waxes mentioned above can be avoided by using natural or chemically modified natural waxes of animal or vegetable origin which also satisfy the demand of growing numbers of consumers for the use of natural, ecologically unobjectionable, i.e. renewable, raw materials.

The most well-known animal wax is beeswax. However, the availability of beeswax as a byproduct of bees is limited. Also, beeswax contains high proportions of esters which can negatively influence the stability of cosmetic compositions containing beeswax.

The commercial vegetable waxes most frequently used in cosmetic compositions at this time are candelilla wax and carnauba wax. However, these waxes are hard and brittle, have a high melting point and are difficult to emulsify in conventional cosmetic compositions.

Candelilla wax and carnauba wax are obtained from the surface of tropical palm leaves whose wax layer is particularly thick, since the plant requires greater protection against loss of water in hot tropical climates than plants indigenous to temperate zones. Because of the comparatively small amount of surface wax of plants growing in temperate climates, the isolation of the surface wax of indigenous plants appears uneconomical, although these plants are available in abundant quantities.

SUMMARY OF THE INVENTION

Therefore, it is an object of the present invention to provide an economical process for obtaining the surface wax of a plant indigenous to temperate zones, a surface wax which does not have the aforementioned disadvantages of waxes conventionally used in cosmetic compositions, and cosmetic compositions containing this surface wax.

The proposed problem is solved in an outstanding manner by the processes according to the invention for obtaining apple wax, by the apple wax obtained by these processes, and by the cosmetic compositions according to the invention containing apple wax.

The subject matter of the present invention is therefore a process for obtaining apple wax in which a) depectinized apple pomace is extracted with a mixture of t-butyl methyl ether and concentrated acetic acid, b) the extract is treated with bleaching clay and water at boiling heat, the t-butyl methyl ether is removed by distillation, the residue is filtered out of the aqueous phase and dried, c) the residue is extracted with t-butyl methyl ether, the extract is reduced until dry, d) the obtained apple wax raw product is then heated with t-butyl methyl ether and bleaching clay, the bleaching clay is removed by filtration and the filtrate is reduced until dry.

The weight ratio in the mixture of t-butyl methyl ether and concentrated acetic acid used in process step a) of the process according to the invention described above for extraction is preferably 10:1 to 100:1, in particular 10:1 to 30:1.

The subject matter of the present invention is further directed to a process for obtaining apple wax in which a) depectinized apple pomace is extracted with a polar solvent, either acetic acid ethyl ester or acetone, b) the obtained extract is then reduced until dry, the obtained apple wax raw product is treated with t-butyl methyl ether, water and bleaching clay at boiling temperature, the t-butyl methyl ether is removed by distillation, the residue is removed from the aqueous phase by filtration and dried, c) the dried residue is extracted with t-butyl methyl ether and the extract is reduced until dry.

The proposed object is also met by a process for obtaining apple wax in which a) depectinized apple pomace is extracted with ethanol, b) the extract is then reduced until dry, the obtained residue is extracted at a pH of at least 8 with a mixture of equal parts of an organic solvent, either acetic acid ethyl ester or acetone, and water, c) the organic phase is then reduced and the obtained apple wax raw product is treated with t-butyl methyl ether, water and bleaching clay at boiling temperature, the t-butyl methyl ether is removed by distillation, the reside is removed from the aqueous phase by filtration and dried, d) the dried residue is extracted with t-butyl methyl ether and the extract is reduced until dry.

The pH of at least 8 of the mixture used for extraction in process step b) of the above-described process for obtaining apple wax is adjusted with bases, e.g. caustic soda, calcium hydroxide, sodium carbonate or potassium carbonate.

Instead of using t-butyl methyl ether, water and bleaching clay, the apple wax raw product obtained in the process according to the invention described above can also be purified by extracting the obtained apple wax raw product with a mixture of t-butyl methyl ether and concentrated acetic acid preferably with a mixture ratio of 10:1 to 100:1, particularly 10:1 to 30:1. The obtained extract is then treated with bleaching clay and water at boiling temperature, the t-butyl methyl ether is then removed and the remaining extract is filtered accompanied by heating. The apple wax obtained by filtration is then dried.

The apple wax obtained according to the preceding process can be purified as follows:

a) apple wax obtained by one of the processes according to the invention described above is absorbed in boiling petroleum ether and the solution is filtered accompanied by heating, b) the filtrate is then treated with bleaching clay at room temperature, the bleaching clay is removed by filtration and the filtrate is reduced until dry.

This process yields a yellowish, odorless apple wax with a dripping point of 54.8° C.

The subject matter of the present invention is also directed to a process for obtaining apple wax in which a) depectinized apple pomace is extracted with supercritical carbon dioxide at a temperature of 32 to 80 degrees Celsius and at a pressure of 100 to 400 bar, b) the extracted product is then dried, dissolved in t-butyl methyl ether, and treated with bleaching clay and water, the t-butyl methyl ether is removed by distillation, and the residue is removed from the aqueous phase by filtration and then dried, and c) the dried residue is then purified with boiling petroleum ether—as described above.

In a particular embodiment form of the process described above, acetic acid may be added to the extraction medium in process step b).

In the preceding process according to the invention, extraction is effected in process step a) with a preferred gas flow rate of 20 kg supercritical carbon dioxide/hour.

The apple wax obtained by the above process according to the invention is a yellowish, odorless wax mass with a dripping point of 55° C.

The proposed object is likewise met by processes for obtaining apple wax in which a) depectinized apple pomace is extracted with ethanol, b) the extract is then reduced until dry, the obtained residue is extracted at a pH of at least 8 with a mixture of equal parts water and an organic solvent selected from acetic acid ethyl ester and acetone, c) the apple wax raw product obtained by reduction of the organic phase is then extracted with supercritical carbon dioxide, d) the obtained extraction product is then dried.

The process according to the invention described above yields a bright yellow, odorless apple wax with a dripping point of 54.5° C.

Cellulose powder, e.g. in the form of a product sold under the trade name Arbocel® by the firm of J. Rettenmaier & Söhne GmbH & Co., Holzmühle, Germany, can be substituted for the bleaching clay used in the processes according to the invention.

In a particular embodiment form of the processes according to the invention, the depectinized apple pomace is ground before extraction.

The IKA Universal Mill M20 by the firm of Janke und Kunkel Ika Werk, Staufen, Germany, can be used to grind small quantities of depectinized apple pomace. After the grinding step, the ground depectinized apple pomace can also be sieved with a commercially available household sieve, if necessary, to ensure a uniform grain size.

The processes, according to the invention, for obtaining apple wax allow the surface wax of the apple to be extracted in an economical manner.

The starting product, depectinized apple pomace, is available at low cost as a waste product of industrial pectin production. The yield of apple wax from depectinized apple pomace is significantly increased compared to the use of pectin-containing apple pomace to obtain apple wax. This increased yield is surprising, since the acidified water used in the conventional method for extracting pectin from apple pomace, as described e.g. in Ullmanns Encyclopädie der technischen Chemie, volume 19, 1980, pages 239–240, is heated above the melting point of the apple wax.

The extraction media, acetone, acetic acid ethyl ester, and particularly ethanol, are unobjectionable in toxicological respects so that the pomace residue can be reused e.g. as fodder for livestock.

In addition, the organic solvents, acetone, acetic acid ethyl ester or ethanol, used for the processes according to the invention can contain quantities of up to 50 percent by weight of water without losses in the yield of apple wax. Therefore, the conventional drying of the depectinized apple pomace resulting after aqueous extraction of pectin from the whole apple pomace can be eliminated in the further processing of the depectinized pomace in one of the processes according to the invention for obtaining apple wax relying on extraction with one of these solvents. In addition to the advantageous savings in energy due to the elimination of the drying step, apple wax produced from undried depectinized apple pomace is not contaminated by caramelizing products which can occur as a result of this drying step.

The subject matter of the present invention is further directed to an apple wax which is obtained by one of the processes according to the invention.

The apple wax which can be obtained by the processes according to the invention has a protective effect on the skin and a less occlusive effect compared to petrolatum which is frequently used in cosmetic compositions. Apple wax is therefore eminently suited as a constituent of cosmetic compositions for the protection and care of the skin.

Apple wax can be used in pure form for covering and for protecting the skin. As a constituent in cosmetic hair care and hair cleaning compositions, apple wax improves wetting and ease of combing as well as the feel of the hair.

Therefore with apple wax, in particular with the apple wax which can be obtained by means of the processes described above, cosmetic means are provided for treating the skin and hair which are distinguished by surprisingly advantageous characteristics and are characterized in that they contain apple wax.

The compositions according to the invention can take the form of preparations for the care or protection of the skin such as face creams for daytime or nighttime application, skin creams, sun-screen creams, lipsticks, lip balms, as well as make-up preparations such as cold cream or rouge, as hair and/or body cleaning compositions such as shampoos, shower-bath preparations, bubble baths or cleansing lotions, as hair treatment preparations such as hair oils, brilliantine or hair waxes, or as hair care compositions such as hair tonics and hair rinses.

When the composition according to the invention is a skin protection or skin care composition in the form of an emulsion, the composition preferably contains 0.05 to 50 percent by weight apple wax.

A skin protection or skin care composition, according to the invention, in the form of an oil-in-water emulsion preferably contains 0.05 to 20 percent by weight apple wax.

A skin protection or skin care composition in the form of a water-in-oil emulsion preferably contains 1 to 50 percent by weight apple wax.

When the composition according to the invention takes the form of a hair cleaning and/or body cleaning composition or a hair care composition, it preferably contains 0.5 to 2 percent by weight apple wax.

Suntan oils according to the invention preferably contain 0.1 to 80 percent by weight apple wax. Hair oils, brilliantine and hair waxes according to the invention preferably contain 1 to 99.8 percent by weight apple wax.

The compositions according to the invention can contain a mixture of apple wax with the physiologically tolerated constituents conventionally used for such preparations, such as carriers and additives.

In a particular embodiment form, the composition according to the invention can contain exclusively apple wax and can be used in this form to cover and protect the skin or as a hair wax.

The composition according to the invention can have an optional preparation form for skin and hair treatment compositions, e.g. an aqueous-alcoholic or alcoholic solution, emulsion, cream or gel. The composition can also be mixed with a propellant or can be sprayed by a pump.

In addition to solvents such as water and lower aliphatic alcohols, e.g. ethanol, propanol and isopropanol, or glycols such as glycerin and 1,2-propylene glycol, conventional additives in solutions, creams, emulsions or gels include wetting agents or emulsifiers from the classes of anionic, cationic, amphoteric or nonionic surface-active substances Such as fatty alcohol sulfates, alkyl benzene sulfonates, alkyl trimethylammonium salts, alkyl betaines, ethoxylated fatty alcohols, ethoxylated nonylphenols, fatty acid alkanolamides, ethoxylated fatty acid esters in quantities of 0.1 to 30 percent by weight, perfume oils in quantities of 0.5 to 5.0 percent by weight, opacifiers such as ethylene glycol distearate in quantities of approximately 0.5 to 5.0 percent by weight, pearlescing agents such as a mixture of fatty acid monoalkylolamide and ethylene glycol distearate in quantities of approximately 1.0 to 10 percent by weight, bactericidal and fungicidal active ingredients such as 2,4,4-trichloro-2-hydroxy diphenyl ether or methyl chloroisothiazolinon in quantities of 0.01 to 1.0 percent by weight, thickeners such as coconut fatty acid diethanolamide in quantities of approximately 0.5 to 3.0 percent by weight, buffer substances such as sodium citrate or sodium phosphate in quantities of 0.1 to 1.0 percent by weight, solubilizers such as ethoxylated castor oil in quantities of approximately 0.1 to 1.0 percent by weight, coloring such as fluorescein sodium salt in quantities of approximately 0.1 to 1.0 percent by weight, nurturing substances such as cationic resins, lanolin derivatives, natural, chemically modified natural, or synthetic waxes and oils such as almond oil, jojoba oil, beeswax, spermaceti in quantities of 0.1 to 5 percent by weight, as well as light stabilizers, moisture-retaining agents, antioxidants, complexing agents and anti-dandruff active ingredients in quantities of approximately 0.01 to 0.8 percent by weight.

The following examples will explain the subject matter of the invention in more detail:

PRODUCTION EXAMPLES

EXAMPLE 1

Preparation of Apple Wax 7.2 kg ground, depectinized apple pomace are extracted with a mixture of 21.6 l t-butyl methyl ether and 1.44 l concentrated acetic acid for 2 hours. After the insoluble apple pomace residue is removed by filtration, the obtained filtrate is mixed with 2.16 kg bleaching clay and 10 l water and is heated for 30 minutes under reflux. The t-butyl methyl ether is then removed by distillation and the precipitate of the apple wax absorbed in the bleaching clay is removed from the remaining aqueous phase by filtration and dried in a vacuum at 40 degrees Celsius. The dried residue is heated in 5 l t-butyl methyl ether for 1 hour under reflux. This is filtered and the filtrate is reduced until dry. 350 g apple wax raw product are obtained and heated under reflux in 11 l t-butyl methyl ether with 1750 g bleaching clay for 1 hour and then filtered while heating. After reducing the filtrate until dry, 340 g apple wax are obtained.

EXAMPLE 2

Preparation of Apple Wax 100 g ground, depectinized apple pomace are extracted in 400 ml acetic acid ethyl ester for 1 hour. After the insoluble apple pomace residue is removed by filtration, the filtrate is reduced until dry. 5.2 g apple wax raw product are obtained. The apple wax raw product is heated with 0.3 l t-butyl methyl ether, 0.14 l water and 30 g bleaching clay for 1 hour under reflux. The t-butyl methyl ether is then removed by distillation and the precipitate is removed from the remaining aqueous phase by filtration and dried in a vacuum at 40 degrees Celsius. The dried precipitate is heated in 300 ml t-butyl methyl ether for 1 hour under reflux. This is filtered and 4.8 g apple wax raw product are obtained by reducing the filtrate until dry.

EXAMPLE 3

Preparation of Apple Wax 100 g ground depectinized apple pomace are heated under reflux in 400 ml acetone for 1 hour. After removing the insoluble apple pomace residue by filtration, the filtrate is reduced until dry. 5.6 g apple wax raw product are obtained and purified with t-butyl methyl ether, water and bleaching clay as in Example 2. 5.17 g apple wax are obtained.

EXAMPLE 4

Preparation of Apple Wax 100 g depectinized apple pomace are heated in 400 ml absolute ethanol for 1 hour under reflux and filtered accompanied by heating. The extract is reduced until dry. 13.8 g of a raw product are obtained which is absorbed in 276 ml acetic acid ethyl ester and 276 ml water. The solution is adjusted with sodium carbonate to a pH of 10, heated for 10 minutes under reflux and then cooled to room temperature. The acetic acid ethyl ester phase is then separated and reduced until dry.

The apple wax raw product remaining as residue of the acetic acid ethyl ester phase is heated with 0.3 l t-butyl methyl ether, 0.14 l water, and 30 g bleaching clay for 1 hour under reflux. The t-butyl methyl ether is removed by distillation, the residue is removed from the remaining aqueous phase by filtration and is dried in a vacuum at 40° C. The dried residue is heated under reflux in 300 ml t-butyl methyl ether for 1 hour. It is then filtered and 4.2 g apple wax are obtained by reducing the filtrate until dry.

EXAMPLE 5

Purification of Apple Wax 600 g apple wax prepared according to Example 1 are heated to boiling in 18 l petroleum ether and filtered while heating. The filtrate is cooled to room temperature, mixed with 1100 g bleaching clay and stirred for 1 hour. The bleaching clay is then removed by filtration and the filtrate is reduced until dry. 230 g odorless, bright-yellow apple wax with a dripping point of 54.8 degrees Celsius are obtained.

EXAMPLE 6

Preparation of Apple Wax 1 kg ground depectinized apple pomace is extracted at 40° C. and at a pressure of 150 bar with supercritical carbon dioxide at a flow rate of 20 kg/h in a first high-pressure vessel for 1 to 2 hours. The charged supercritical carbon dioxide is then transferred to a second high-pressure vessel and expanded to atmospheric pressure. The resulting solid residue is separated and dried in a vacuum at 40° C.

100 g of the dried residue are then dissolved in 1 l t-butyl methyl ether. After filtering the solution, 150 g bleaching clay and 300 ml water are added and the mixture is heated for 15 minutes under reflux. The t-butyl methyl ether is then removed by distillation and the wax absorbed in the bleaching clay is filtered out of the remaining aqueous phase as residue and dried at 40° C. in a vacuum. The dried residue is then washed five times with 0.5 l boiling petroleum ether in each instance. By reducing the purified petroleum ether phases until dry, 38 g odorless, bright-yellow apple wax are obtained with a dripping point of 55° C.

EXAMPLE 7

Preparation of Apple Wax 1000 g depectinized apple pomace are heated under reflux for 1 hour in 4 l absolute ethanol and filtered accompanied by heating. The extract is reduced until dry. 138 g of a raw product are obtained and absorbed in 2.76 l acetic acid ethyl ester and 2.76 l water. The solution is adjusted with sodium carbonate to pH=10, heated under reflux for 10 minutes, and then cooled to room temperature. The acetic acid ethyl ester phase is then separated and reduced until dry.

The obtained residue is extracted at 40° C. and a pressure of 150 bar with supercritical carbon dioxide at a flow rate of 20 kg/h in a first high-pressure vessel for 1.5 hours. The charged supercritical carbon dioxide is then transferred to a second high-pressure vessel, cooled to room temperature, and expanded to atmospheric pressure.

The resulting solid residue is separated and dried in a vacuum at 40° C. 380 g yellowish, odorless apple wax with a dripping point of 54.5° C. are obtained.

| Examples for Cosmetic Compositions | |
|---|---|
| Example I: | Skin cream with protective action |
| 2.00 g | apple wax |
| 8.00 g | glycerin stearate, self-emulsifying |
| 2.00 g | mixture of glyceryl hydroxystearate, cetyl palmitate, microcrystalline wax and trihydroxystearin |
| 1.00 g | stearin |
| 8.00 g | paraffinium perliquidum |
| 0.10 g | p-hydroxybenzoic acid propyl ester |
| 0.20 g | p-hydroxybenzoic acid methyl ester |
| 0.05 g | allantoin |
| 0.20 g | perfume |
| 78.45 g | water |
| 100.00 g | |

| Example II: | Skin cream with protective action |
|---|---|
| 4.00 g | apple wax |
| 8.00 g | glycerin stearate, self-emulsifying |
| 1.00 g | stearin |
| 8.00 g | liquid paraffin |
| 0.10 g | p-hydroxybenzoic acid propyl ester |
| 0.20 g | p-hydroxybenzoic acid methyl ester |
| 0.05 g | allantoin |

| Examples for Cosmetic Compositions | |
|---|---|
| 0.20 g | perfume |
| 78.45 g | water |
| 100.00 g | |

EXAMPLE III

Comparison Tests for Skin Protection Action

The skin cream according to Example I was applied to an area of 2 cm² on the skin of the right inside underarm of 10 test participants and the skin cream according to Example II was applied to another area of 2 cm² on the skin of the same underarm and rubbed in lightly for 1 minute. The excess skin cream was then removed by lightly dabbing with cellulose material. The left underarm of the test participants remained untreated for the time being.

The skin temperature of the two skin surfaces of the right underarm treated with the skin creams according to Examples I and II and of an untreated skin surface of the left underarm was measured with an infrared radiation thermometer KT15 by the firm of Heimann GmbH, Wiesbaden, lens L, with an equal distance of the lens from the surface of the skin and constant ambient temperature.

A 4-percent aqueous ammonia solution was then applied to the area of 2 cm² on the skin treated with the skin creams according to Example I and Example II and to a previously untreated surface of the same size on the left underarm of the test participants. After 10 minutes, the skin temperature was determined again in the manner described previously. The average increase in temperature was then calculated from the temperatures measured on the right and left underarm of the 10 test participants before and after treatment with ammonia and compiled in the following table.

| Treated with | Average of increase in skin temperature |
|---|---|
| 1. skin cream of Example I | 1.06 ± 1.38 degrees Celsius |
| 2. ammonia solution control | 1.33 ± 0.75 degrees Celsius |
| 1. ammonia solution | |
| 1. Skin cream of Example 2 | 1.14 ± 1.22 degrees Celsius |
| 2. ammonia solution control | 1.30 ± 0.73 degrees Celsius |
| 1. ammonia solution | |

The comparison tests show that by applying the skin creams according to Examples I and II beforehand, the increase in skin temperature caused by the ammonia is reduced and they accordingly have a skin protecting action.

| Example IV | Shampoo |
|---|---|
| 11.20 g | mixture of sodium lauryl ether sulfate and salicylic acid |
| 1.50 g | triglycol distearate |
| 0.50 g | apple wax, produced according to Example 4 |
| 4.20 g | sodium chloride |
| 82.60 g | water |
| 100.00 g | |

The shampoo produces a silky foam and improves the ease of combing and the feel of the hair washed with it.

| Example V | Hair tonic composition |
|---|---|
| 3.500 g | cetyl stearyl alcohol |
| 0.500 g | apple wax, produced according to Example 5 |
| 0.550 g | cetyl trimethyl ammonium chloride |
| 0.004 g | coloring |
| 0.200 g | vegetable extract (Extrapon 5 Special) |
| 0.500 g | citric acid |
| 0.900 g | perfume oil |
| 93.846 g | water |
| 100.000 g | |

The hair tonic composition can be rinsed out of the hair easily after application, provides good wetting and ease of combing and gives the hair a good feel and a groomed appearance.

| Example VI | Hair tonic composition |
|---|---|
| 2.360 g | cetyl stearyl alcohol |
| 0.900 g | lauryl alcohol diglycol ether |
| 1.240 g | petrolatum |
| 1.000 g | apple wax |
| 10.000 g | betaine monohydrate |
| 0.378 g | cetyl stearyl sulfate sodium salt |
| 0.150 g | D,L-mandelic acid (D,L-hydroxyphenylacetic acid) |
| 0.150 g | salicylic acid |
| 2.000 g | citric acid |
| 0.300 g | perfume |
| 81.522 g | water |
| 100.000 g | |

The hair tonic composition can be rinsed out of the hair easily after application, provides good wetting and ease of combing and gives the hair a good feel and a groomed appearance.

| Example VII | Lip balm stick |
|---|---|
| 25.00 g | castor oil |
| 5.00 g | jojoba oil |
| 20.00 g | mineral oil |
| 25.00 g | microcrystalline wax |
| 15.00 g | decyl oleate |
| 8.00 g | apple wax |
| 1.70 g | phenyltrimethicone |
| 0.30 g | perfume |
| 100.00 g | |

| Example VIII | Sun-protection cream (oil-in-water emulsion) |
|---|---|
| 8.00 g | glyceryl stearate |
| 2.00 g | cetyl stearyl alcohol |
| 1.50 g | cetyl stearyl alcohol ethoxylated with 20 moles ethylene oxide |
| 1.50 g | cetyl stearyl alcohol ethoxylated with 12 moles ethylene oxide |
| 3.00 g | apple wax |
| 6.00 g | mixed triesters of glycerin with capric acid and caprylic acid |
| 8.00 g | mixture of esters of capric acid and caprylic acid with coconut alcohol |
| 6.00 g | dibutyl adipate |
| 4.00 g | octyl dodecanol |
| 3.00 g | dimethylpolysiloxane |
| 4.00 g | light stabilizing filter |
| 2.58 g | glycerin |
| 50.42 g | water |
| 100.00 g | |

All percentages indicated in the present Application represent percent by weight.

We claim:

1. Composition for treating skin and hair, said composition consisting of 0.5 to 2 percent by weight of apple wax, 0.1 to 30 percent by weight of at least one surfactant, a solvent selected from the group consisting of water, ethanol, propanol, isopropanol, glycols and mixtures thereof and at least one additive selected from the group consisting of perfume oils; opacifiers; pearlescing agents; bacterial and fungicidal ingredients; coconut fatty acid diethanolamide; buffer substances; coloring materials; solubilizers; light stabilizers; antioxidants; complexing agents and antidandruff active ingredients.

2. Composition as defined in claim 1, in the form of a solution, an emulsion, a cream, or a gel.

3. Composition as defined in claim 1, wherein said at least one surfactant is selected from the group consisting of anionic, cationic, amphoteric and nonionic surfactants.

* * * * *